United States Patent
Tani et al.

(10) Patent No.: US 7,414,075 B2
(45) Date of Patent: Aug. 19, 2008

(54) COMPOSITION FOR LOWERING INTERNAL LIPID CONTENT

(75) Inventors: Yumiko Tani, Nagoya (JP); Tatsuo Watanabe, Shizuoka (JP); Masanori Kamei, Yokohama (JP); Masatoshi Kato, Yokohama (JP); Koji Yanae, Yokohama (JP)

(73) Assignee: Ajinomoto Co., Inc., Tokyo (JP)

( * ) Notice: Subject to any disclaimer, the term of this patent is extended or adjusted under 35 U.S.C. 154(b) by 655 days.

(21) Appl. No.: 11/107,745

(22) Filed: Apr. 18, 2005

(65) Prior Publication Data

US 2005/0239883 A1  Oct. 27, 2005

Related U.S. Application Data

(63) Continuation of application No. PCT/JP2004/006538, filed on May 14, 2004.

(30) Foreign Application Priority Data

May 15, 2003  (JP)  ............................. 2003-137317

(51) Int. Cl.
    *A61K 31/22*  (2006.01)
    *A61K 31/23*  (2006.01)
(52) U.S. Cl. ................ 514/546; 514/549; 514/552
(58) Field of Classification Search ................ None
    See application file for complete search history.

(56) References Cited

FOREIGN PATENT DOCUMENTS

| JP | 9-13075 | 1/1997 |
|----|---------|--------|
| JP | 9-23817 | 1/1997 |
| JP | 9-30962 | 2/1997 |
| JP | 2001-26538 | 1/2001 |
| JP | 2002-114676 | 4/2002 |
| WO | 02/17906 | 3/2002 |

OTHER PUBLICATIONS

Iwai, K., et al., "Roles as metabolic regulators of the non-nutrients, capsaicin and capsiate, supplemented to diets," Proc. Japan Acad. 2003;79(7):207-212.

Kobata, K., et al., "Novel Capsaicinoid-like Substances, Capsiate, and Dihydrocapsiate, from the Fruits of a Nonpungent Cultivar, CH-19 Sweet, of Pepper (*Capsicum annuum* L.)" J. Agric. Food Chem. 1998;46(5):1695-1697.

Kobata, K., et al., "Nordihydrocapsiate, a New Capsinoid from the Fruits of a Nonpungent Pepper, *Capsicum annuum*, " J. Nat. Prod. 1999;62:335-336.

Masuda, Y., et al., "Upregulation of uncoupling proteins by oral administration of capsiate, a nonpungent capsaicin analog," J. Appl. Physiol. 2003;95:2408-2415.

New Food Industry 2003;45(2):17-23.

Nanzando Igaku Daijiten (Gokaban), Jan. 16, 1998, p. 660.

Ohnuki, K., et al., "CH-19 Sweet, Nonpungent Cultivar of Red Pepper, Increased Body Temperature in Mice with Vanilloid Receptors Stimulation by Capsiate," J. Nutr. Sci. Vitaminol. 2001;47:295-298.

Sancho, R., et al., "Immunosuppressive activity of capsaicinoids: capsiate derived from sweet peppers inhibits NF-κB activation and is a potent anti-inflammatory compound in vivo," Eur. J. Immunol. 2002;32:1753-1763.

International Search Report for PCT Patent Appl. No. PCT/JP2004/006538 (Jun. 22, 2004).

*Primary Examiner*—Raymond J Henley, III
(74) *Attorney, Agent, or Firm*—Shelly Guest Cermak; Cermak Kenealy & Vaidya LLP

(57) ABSTRACT

A composition for lowering internal lipid in a subject which contains a capsinoid substance represented by the following formula

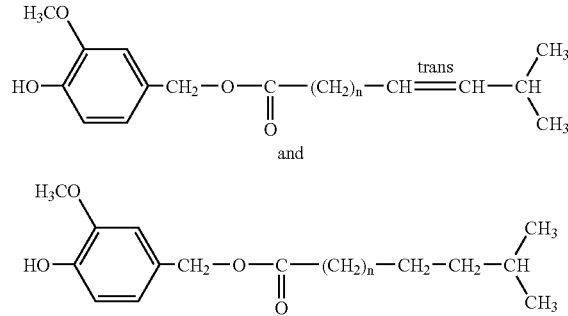

wherein n is an integer from 0 to 10. Methods of using the compositions are disclosed and include administering to a subject in need of such treatment.

25 Claims, No Drawings

COMPOSITION FOR LOWERING INTERNAL LIPID CONTENT

This application claims the benefit of PCT/JP2004/006538 filed May 14, 2004 under 35 U.S.C. §120 as a continuation.

FIELD OF THE INVENTION

The present invention relates to a composition which contains capsinoid compounds. Such compositions are useful for lowering the internal lipid level in a subject.

BRIEF DESCRIPTION OF THE RELATED ART

Yazawa et al. have reported selectively fixing a new species of chili pepper, called CH-19-sweet, which is not pungent. This new species was derived from self-progeny of "CH-19," which is a species of hot chili pepper from Thailand. It was found that the CH-19-sweet contains nearly no capsaicinoid, but does contain a large amount of novel capsinoid compounds which are fatty acid esters of vanillyl alcohol. Yazawa et al. also confirmed that these capsinoid compounds are present in common local species of hot chili pepper such as "Nikko" and "Goshiki" (see Yazawa et al., *Engei Gakkai Zasshi*, Vol. 58, pp. 601-607 (1989)).

Yazawa, et al. have further reported that these capsinoid compounds are not pungent and have specific functions, such as immune-stimulation activity and causing an increase in body surface temperature (see JP-A-11-246478). The present applicants have disclosed that these capsinoid compounds have an anti-obesity effect (see JP-A-2001-26538) and an endurance-improving effect (see JP-A-2002-114676).

Capsaicinoid compounds can also have a part of various physiological effects similar to the capsinoid compounds as mentioned above. As seen in the significant difference in pungency, capsinoid is not believed to have the same physiological action as capsaicinoid. Particularly, capsaicinoid has been reported to not suppress a rise of hepatic fat (Kawada et al., *J. Nutr.*, Vol. 116, pp. 1272-1278 (1986), Table 2 on p. 1274.)

In addition, capsinoid compounds' influence on serum cholesterol has not been previously reported.

SUMMARY OF THE INVENTION

As mentioned above, capsinoid and capsaicinoid do not always have the same physiological action because of the difference in their structures; therefore, finding a new physiological action of capsinoid is desirable. Furthermore, since capsinoid is devoid of pungency, its formulation with foods, drugs, etc. is easy. Confirmation of the physiological action of capsinoid is desirable.

Thus, an object of the present invention is to clarify a novel physiological action of capsinoid compounds and to apply it to various uses.

It has now been found that capsinoid compounds suppress an increase in serum cholesterol and hepatic fat, or internal lipids, or decrease a lipid level thereof.

Accordingly, it is an object of the present invention to provide a composition comprising capsinoid compounds selected from the group consisting of

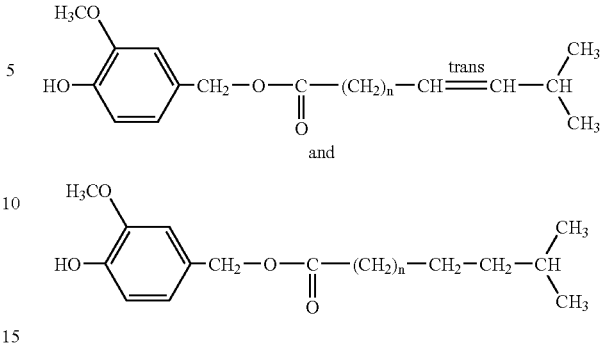

and wherein n is an integer from 0 to 10.

It has been particularly shown that the capsinoid of the present invention improves an arteriosclerosis index because it significantly lowers total cholesterol in the serum and may be used for prevention or treatment of arteriosclerosis.

Accordingly, it is a further object of the present invention to provide the composition as described above, wherein the composition lowers the total serum cholesterol amount and improves the arteriosclerosis index in a subject.

Among the capsinoid compounds represented by the general formula above, the compound where n is 3, 4 or 5 is preferred, and it is particularly preferred that the compound is 4-hydroxy-3-methoxybenzyl (E)-8-methyl-6-nonenoate or 4-hydroxy-3-methoxybenzyl 8-methylnonanoate.

Accordingly, it is a further object of the present invention to provide the composition as described above, wherein n is 3, 4 or 5.

It is a further object of the present invention to provide the composition as described above, wherein the capsinoid compound is 4-hydroxy-3-methoxybenzyl (E)-8-methyl-6-nonenoate or 4-hydroxy-3-methoxybenzyl 8-methylnonanoate.

Capsinoid compounds are found in chili pepper plants, which are popular to eat. Therefore, when it is formulated as food or beverage, it is not necessary to purify and isolate the capsinoid compounds, but they can be present as a plant or fruit of a plant containing the same. In that case, fruit or the like derived from a chili pepper species CH-19-sweet, which contains large amounts of said compounds may be advantageously used.

Accordingly, it is a further object of the present invention to provide the composition as described above, wherein the capsinoid compounds are derived from a plant or a fruit of a plant It is also possible that the capsinoid compounds are advantageously formulated as an extract from the above plant or fruit.

Accordingly, it is a further object of the present invention to provide the composition as described above, wherein the capsinoid compound is derived from an extract of a plant or fruit of a plant.

It is a further object of the present invention to provide the composition as described above, wherein the plant or the fruit is derived from a chili pepper species CH-19-sweet.

The composition of the present invention can be formulated as a food, beverage, or drug and, particularly since the capsinoid compound is devoid of pungency.

Accordingly, it is a further object of the present invention to provide a drug comprising the composition as described above.

It is a further object of the present invention to provide a method of lowering internal lipid levels in a subject by administering the composition as described above.

It is a further object of the present invention to provide the method as described above, wherein said internal lipid is selected from the group consisting of serum cholesterol and hepatic fat.

It is a further object of the present invention to provide a method of treating arthrosclerosis in a subject comprising administering to the subject the composition as described above.

DESCRIPTION OF THE PREFERRED EMBODIMENTS

Until now, there has been no report that capsinoid lowers hepatic fat levels. The present invention discloses for the first time that capsinoid has such a specific physiological action. It is to be particularly noted that, although capsaicinoid and capsinoid have been known to lower a triglyceride concentration in blood, capsaicinoid has been believed not to decrease hepatic fat level in general as shown in Kawada et al. (*J. Nutr*, Vol. 116, pp. 1272-1278). However, the present inventors have now clarified for the first time that capsinoid also suppresses an increase in the hepatic fat.

With regard to capsinoid, it has not been previously reported that an arteriosclerosis index could be improved by lowering serum cholesterol levels. Consequently, and in accordance with the present invention, there is provided a capsinoid compound is devoid of pungency, a novel composition for lowering serum cholesterol, improving the arteriosclerosis index, and lowering hepatic fat in a subject. This novel composition may be easily formulated in food or drugs.

The capsinoid compounds of the present invention can be prepared by purification and separation from a plant and/or the fruit of a plant belonging to genus *Capsicum* (hereinafter, "chili pepper"). Chili peppers may be common hot chili peppers, such as "Nikko" and "Goshiki." Any kind of chili pepper may be used for purifying the capsinoid compounds as long as it contains capsinoid compounds. Examples of these include common non-pungent chili pepper species such as CH-19-sweet, "Manganji," "Fushimi Amanaga," small sweet peppers, green peppers, etc., and since these contain capsinoid compounds in large quantities, these can be advantageously used. CH-19-sweet, a non-pungent species, is particularly preferred since it has a high amount of capsinoid. The term CH-19-sweet includes CH-19-sweet, similar species derived from CH-19-sweet, and progeny derived from "CH-19 sweet."

Purification and separation can be carried out by well-known techniques to persons skilled in the art, such as extraction with solvent, various chromatographies including silica gel chromatography, preparative high-performance liquid chromatography, etc., either solely or appropriate combinations thereof. For example, the method disclosed in JP-A-11-246478 may be used.

The capsinoid compounds of the present invention may also be synthesized by transesterification using the corresponding fatty acid ester and vanillyl alcohol as disclosed, for example, in JP-A-11-246478. Alternatively, it is also possible to synthesize by other reaction means known to persons skilled in the art based on the structural formula. Also, the capsinoid compounds of the present invention can be easily prepared synthetically using an enzyme. For example, a reverse reaction of lipase utilizing a compound such as triglyceride having fatty acid ester and/or fatty acid corresponding to the desired compound and vanillyl alcohol, and a desired capsinoid compound can be prepared. Details of this method are disclosed in JP-A-2000-312598.

The capsinoid compounds of the present invention are not necessarily purified, separated, or synthesized in a pure form, but may include parts or extracts of the plant and/or fruit of a chili pepper species CH-19-sweet, either dried or grinded, or crudely extracted substance thereof.

Thus, the chili pepper species CH-19-sweet rarely contains a capsaicinoid which is pungent or invasive, but does contain a large amount of capsinoid (fatty acid ester of vanillyl alcohol) which has no pungency. Therefore, it does not demonstrate the pungency and invasive properties typical of a common chili pepper. Accordingly, the capsinoid compounds of the present invention can be advantageously formulated with food, food additives, feed, or particularly, with drugs. Drug formulations containing the capsinoid compounds of the present invention can be formulated for oral administration either directly or merely by simple physical and/or chemical treatments such as drying, grinding, and crude extraction. The term "a plant or fruit of a plant" includes the plant and/or fruit per se, or a product prepared from the plant or fruit by simple physical and/or chemical treatment, such as drying, grinding, and crude extraction thereof.

The compositions of the present invention are useful in suppressing a rise in serum cholesterol and hepatic fat, or in lowering the internal lipid level thereof. Such a composition may be administered either orally or parenterally and, as mentioned above, since the capsinoid compound of the present invention is not pungent, it is particularly suitable for oral administration.

When the composition of the present invention is clinically used as a pharmaceutical composition, it may be formulated into various preparations by the addition of pharmaceutically acceptable additives, depending upon the dosage form. Various pharmaceutically acceptable additives which are commonly used in the field of pharmaceutical preparations may be used, and examples thereof include gelatin, lactose, sugar, titanium oxide, starch, crystalline cellulose, hydroxypropyl methyl cellulose, carboxymethyl cellulose, corn starch, microcrystalline wax, white Vaseline, magnesium metasilicate aluminate, anhydrous calcium phosphate, citric acid, trisodium citrate, hydroxypropyl cellulose, sorbitol, sorbitan fatty acid ester, polysorbate, sucrose fatty acid ester, polyoxyethylene hydrogenated castor oil, polyvinylpyrrolidone, magnesium stearate, light silicic acid anhydride, talc, vegetable oil, benzyl alcohol, alabic gum, propylene glycol, polyalkylene glycol, cyclodextrin, and hydroxypropyl cyclodextrin.

Examples of the preparation form are solid preparations such as tablets, capsules, granules, diluted powders, and suppositories; and liquid preparations such as syrup, elixirs, and injections. They may be prepared by common methods typically used in the field of pharmaceutical preparations. Liquid preparations may be dissolved or suspended in water or in another appropriate medium upon use. Particularly in the case of injections, the preparation may also be dissolved or suspended in a physiological saline solution or a glucose solution or may have buffer or preservative added.

The preparation may contain the capsinoid compound of the present invention in an amount of 1 to 100% by weight or, preferably, 10 to 80% by weight for all drug preparations.

When the capsinoid compounds of the present invention are used in a clinical field, the dose and frequency of administration may vary depending on the subject's gender, age, body weight, and degree of symptoms, type and range of the desired treatment, etc. Typically, it is preferred to administer 1 to 50 mg/kg per day for an adult either once per day, or split into several doses a day when of orally administered.

The capsinoid compounds of the present invention can be freely mixed with various foods, such as those of solid, liquid, sol, gel, powder, or granules. Mixing and formulating food containing the composition of the present invention may be carried out by any method which is known in the relevant art. Formulating with solids such as chocolate, liquids such as sports drink and retort pouch such as adzuki porridge may be easily conducted by a method disclosed, for example, in JP-A-11-246478.

The capsinoid compounds of the present invention may be also used as food additives. A food additive containing the capsinoid compounds of the present invention may be manufactured by a method which is known to persons skilled in the art, such as making a capsinoid composition into granules or capsules, for example, and adding various excipients such as dextrin, corn starch, lactose, and an auxiliary material such as emulsifier. If desired, a preservative, flavor, etc. may be added thereto.

It is not necessary that the capsinoid compounds contained in the food be purified to a particular degree. Thus, CH-19-sweet per se (non-treated substance) which is a fixed species of chili pepper having no pungency as mentioned above, a dried product (grinded product) thereof, or an extract of CH-19-sweet with various kinds of solvents commonly used for extraction from natural substances in the relevant art, such as alcohols including ethyl acetate, ethanol, or an emulsifier solution appropriate for food.

The capsinoid compounds of the present invention may be freely formulated with various feeds such as those in a form of solid, liquid, sol, gel, powder, and granules. Persons skilled in the art will easily understand that such a formulation can be achieved by using methods substantially identical with the formulation of food, or by modifying the same in an appropriate manner.

The above-mentioned CH-19-sweet which is a fixed species of non-pungent chili pepper has been registered at the Control Center for Seeds and Seedlings, Ministry of Agriculture, Forestry and Fisheries as No. 10375 and is available from that organization.

The present invention will now be illustrated in detail by way of the following non-limiting Examples.

EXAMPLES

Administration of Test Compound:

Twenty-four nine-week old male Wistar strain rats were used and divided into four groups each comprising six rats, including a control group, a 0.1 mmol/kg capsaicin group, a 0.1 mmol/kg capsinoid group, and a 1.0 mmol/kg capsinoid group. A 20% lard food to which 1% cholesterol was added was administered as a feed to the control group. For the remaining three groups, capsaicin of 0.1 mmol per kg final concentration of the feed, capsinoid of 0.1 mmol per kg final concentration of the feed, and capsinoid of 1.0 mmol per kg final concentration of the feed, respectively, were added to the feed, similar to the control group. The capsinoid was a mixture of 4-hydroxy-3-methoxybenzyl (E)-8-methyl-6-nonenoate and 4-hydroxy-3-methoxybenzyl 8-methylnonanoate in about 2:1 ratio.

The above groups each comprising six rats were subjected to pair feeding for four weeks. Breeding of the experimental animals was conducted in each individual cage and, during the breeding period, body weight was measured once a week and ingested amount of the feed was calculated by deducting the residue from the administered amount. Feces were collected for three days before dissection. After completion of breeding, the rats were sacrificed and dissected. Blood was collected. The liver, the fat around the kidney, and the fat around the epididymis were each separately excised and weighed. Furthermore, the ratio of the excised organs to the total body weight was calculated. The detailed breeding process is shown in Table 1. The excretion rate of cholesterol into the feces during the three days before sacrifice and dissection is shown in Table 2. The ratios of organ weight to total body weight are shown in Table 3. Unless otherwise mentioned, the results in the following tables are shown in terms of mean value±standard deviation and, statistically, test of significance was conducted at $p<0.05$ by ANOVA and Duncan's multiple range test. In the tables, * means $p<0.05$.

Table 1

TABLE 1

Process of Breeding
Rate of Increase in Body Weight and Average Ingested Amount of Feed

| | Body Weight (g) on Initial Day of Test | Body Weight (g) on Final Day of Breeding | Percentage Increase in Body Weight | Average Ingested Amount (g) of Feed | Body Weight (g) on Dissected Day |
|---|---|---|---|---|---|
| Control Group | 289 ± 5 | 372 ± 21 | 129 ± 5 | 16.5 ± 0.8 | 365 ± 17 |
| 0.1 mmol/kg Capsaicin Group | 295 ± 8 | 392 ± 11 | 133 ± 4 | 17.0 ± 1 | 367 ± 12 |
| 0.1 mmol/kg Capsinoid Group | 287 ± 3 | 368 ± 12 | 128 ± 4 | 16.5 ± 0.5 | 360 ± 12 |
| 1.0 mmol/kg Capsinoid Group | 280 ± 7 | 358 ± 8 | 128 ± 4 | 16.9 ± 0 | 358 ± 7 |

Table 2

TABLE 2

Excreted Rate of Cholesterol into Feces during Three Days

| | Excreted Amount of Feces (g/3 days) | Ingested Amount of Feed (g/3 days) | Ingested Amount of Cholesterol (mg/3 days) | Cholesterol in Feces Excreted Amount (mg/3 days) | Excreted Rate (%) |
|---|---|---|---|---|---|
| Control Group | 3.4 ± 0.3 | 49.0 ± 2.4 | 490 ± 24 | 229 ± 14 | 46.7 ± 2.7 |
| 0.1 mmol/kg Capsaicin Group | 3.3 ± 0.4 | 49.3 ± 3.1 | 493 ± 31 | 240 ± 27 | 48.6 ± 3.4 |
| 0.1 mmol/kg Capsinoid Group | 4.0 ± 0.8* | 49.5 ± 1.4 | 495 ± 14 | 248 ± 34 | 50.0 ± 6.0 |
| 1.0 mmol/kg Capsinoid Group | 3.6 ± 0.3 | 50.6 ± 0.0 | 506 ± 0 | 236 ± 7 | 46.7 ± 1.4 |

TABLE 3

Ratio of the Weight of Organ to Total Body Weight

| | Liver (g) | Liver (%) | Fat (g) around Kidney | Fat (%) around Kidney | Fat (g) around Epididymis | Fat (%) around Epididymis |
|---|---|---|---|---|---|---|
| Control Group | 15.9 ± 2.1 | 4.4 ± 0.5 | 4.2 ± 1.1 | 1.2 ± 0.3 | 4.8 ± 0.7 | 1.3 ± 0.3 |
| 0.1 mmol/kg Capsaicin Group | 14.4 ± 0.9 | 3.9 ± 0.1* | 3.8 ± 0.6 | 1.0 ± 0.1 | 4.6 ± 0.5 | 1.3 ± 0.1 |
| 0.1 mmol/kg Capsinoid Group | 15.0 ± 1.2 | 4.1 ± 0.2 | 3.6 ± 1.1 | 1.0 ± 0.3 | 4.5 ± 0.7 | 1.3 ± 0.2 |
| 1.0 mmol/kg Capsinoid Group | 16.0 ± 1.4 | 4.5 ± 0.4 | 3.5 ± 0.5 | 1.0 ± 0.1 | 4.3 ± 0.5 | 1.2 ± 0.1 |

Example 1

Influence on Serum Cholesterol and Arteriosclerosis Index

Blood was collected from the experimental animals bred as above and total cholesterol (T-chol) and HDL cholesterol (HDL-chol) in the serum was measured. More specifically, total cholesterol and HDL cholesterol were measured according to a method disclosed in "Akiko Tsujihara and Yumiko Tani: Influence of yucca saponin and pure konjak powder on lipid metabolism of rats fed with a high-fat and high-cholesterol feed: *Eiyo Shokuryo Gakkaishi*, vol. 51, pp. 157-163 (1998)". The Arteriosclerosis index was calculated by (T-chol-HDL-chol)/(HDL-chol). The results are shown in Table 4, including the amount of triglyceride in the serum (TG).

Table 4

TABLE 4

Result of Measurement of Cholesterol in Serum

| | T-chol (mg/dl) | HDL-chol (mg/dl) | Arteriosclerosis Index | TG (mg/dl) |
|---|---|---|---|---|
| Control Group | 88.7 ± 4.4 | 41.1 ± 4.4 | 1.2 ± 0.4 | 49.4 ± 7.4 |
| 0.1 mmol/kg Capsaicin Group | 71.2 ± 8.1* | 34.2 ± 6.5* | 1.2 ± 0.4 | 25.5 ± 5.3* |
| 0.1 mmol/kg Capsinoid Group | 62.5 ± 6.6* | 36.3 ± 2.4 | 0.7 ± 0.2* | 40.7 ± 4.8* |

From the above result, the capsinoid compound of the present invention significantly lowers the total cholesterol in serum and also significantly improves the arteriosclerosis index.

Example 2

Influence on Hepatic Fat

The experimental animals bred as above were sacrificed and dissected. Amounts of total lipid (T-lipid), cholesterol (Chol), and triglyceride (TG) in the excised liver were measured. Measurements were conducted again according to a method disclosed in "Akiko Tsujihara and Yumiko Tani: Influence of yucca saponin and pure konjak powder on lipid metabolism of rats fed with a high-fat and high-cholesterol feed: *Eiyo Shokuryo Gakkaishi*, vol. 51, pp. 157-163 (1998)".

The result is shown in Table 5.

Table 5

TABLE 5

Result of Measurement of Hepatic Fat

| | T-lipid (g/100 g) | Chol (g/100 g) | TG (g/100 g) |
|---|---|---|---|
| Control Group | 31.5 ± 1.7 | 8.8 ± 0.6 | 13.6 ± 0.7 |
| 1.0 mmol/kg Capsinoid Group | 24.3 ± 1.5* | 7.1 ± 0.7* | 7.3 ± 0.5* |

From the above result, it is noted that the capsinoid compound of the present invention significantly lowers the hepatic fat (hepatic lipid).

As mentioned hereinabove, it is now apparent that the capsinoid compound of the present invention significantly lowers the total cholesterol level in serum, improves the arteriosclerosis index, and even lowers or suppresses the rise in hepatic fat level. Consequently, the compound of the present invention may be very advantageously formulated as a composition for such a use.

While the invention has been described in detail with reference to preferred embodiments thereof, it will be apparent to one skilled in the art that various changes can be made, and equivalents employed, without departing from the scope of the invention. Each of the aforementioned documents, including the foreign priority document JP2003-137317, is incorporated by reference herein in its entirety.

We claim:

1. A method of lowering the internal lipid in a subject comprising administering a composition comprising at least one capsinoid compound selected from the group consisting of:

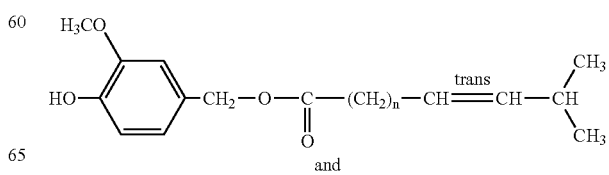

and

-continued

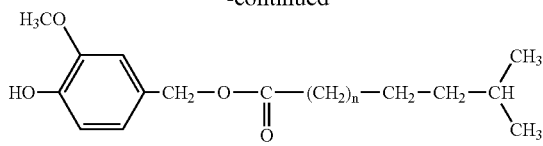

wherein n is an integer from 0 to 10.

2. The method according to claim 1, wherein said composition lowers total serum cholesterol and improves the arteriosclerosis index.

3. The method according to claim 1, wherein n is selected from the group consisting of 3, 4, and 5.

4. The method according to claim 1, wherein said capsinoid compound is selected from the group consisting of 4-hydroxy-3-methoxybenzyl (E)-8-methyl-6-nonenoate and 4-hydroxy-3-methoxybenzyl 8-methylnonanoate.

5. The method according to claim 1, wherein said capsinoid compound is derived from a plant or a fruit of a plant.

6. The method according to claim 5, wherein said plant or said fruit is CH-19-sweet.

7. The method according to claim 1, wherein said capsinoid compound is derived from an extract of a plant or a fruit of a plant.

8. The method according to claim 7, wherein said extract is derived from CH-19-sweet.

9. A method of reducing the hepatic fat in a subject comprising administering a composition comprising at least one capsinoid compound selected from the group consisting of:

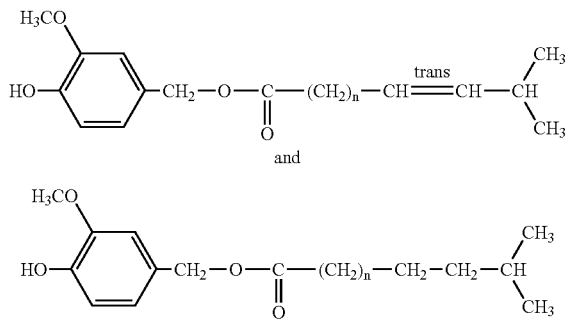

wherein n is an integer from 0 to 10.

10. The method according to claim 9, wherein said composition lowers total serum cholesterol and improves the arteriosclerosis index.

11. The method according to claim 9, wherein n is selected from the group consisting of 3, 4, and 5.

12. The method according to claim 9, wherein said capsinoid compound is selected from the group consisting of 4-hydroxy-3-methoxybenzyl (E)-8-methyl-6-nonenoate and 4-hydroxy-3-methoxybenzyl 8-methylnonanoate.

13. The method according to claim 9, wherein said capsinoid compound is derived from a plant or a fruit of a plant.

14. The method according to claim 13, wherein said plant or said fruit is CH-19-sweet.

15. The method according to claim 9, wherein said capsinoid compound is derived from an extract of a plant or a fruit of a plant.

16. The method according to claim 15, wherein said extract is derived from CH-19-sweet.

17. A method of reducing the serum cholesterol in a subject comprising administering a composition comprising at least one capsinoid compound selected from the group consisting of:

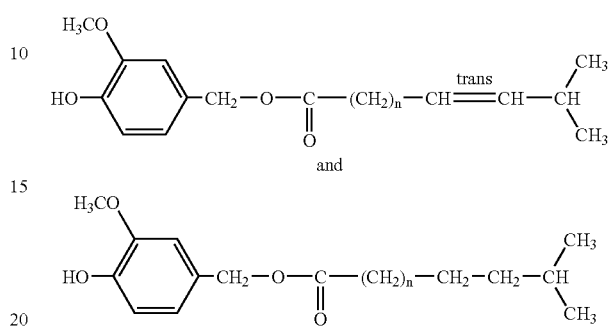

wherein n is an integer from 0 to 10.

18. The method according to claim 17, wherein said composition improves the arteriosclerosis index.

19. The method according to claim 17, wherein n is selected from the group consisting of 3, 4, and 5.

20. The method according to claim 17, wherein said capsinoid compound is selected from the group consisting of 4-hydroxy-3-methoxybenzyl (E)-8-methyl-6-nonenoate and 4-hydroxy-3-methoxybenzyl 8-methylnonanoate.

21. The method according to claim 17, wherein said capsinoid compound is derived from a plant or a fruit of a plant.

22. The method according to claim 21, wherein said plant or said fruit is CH-19-sweet.

23. The method according to claim 17, wherein said capsinoid compound is derived from an extract of a plant or a fruit of a plant.

24. The method according to claim 23, wherein said extract is derived from CH-19-sweet.

25. A method of treating arthrosclerosis in a subject comprising administering to the subject the composition comprising at least one capsinoid compound selected from the group consisting of:

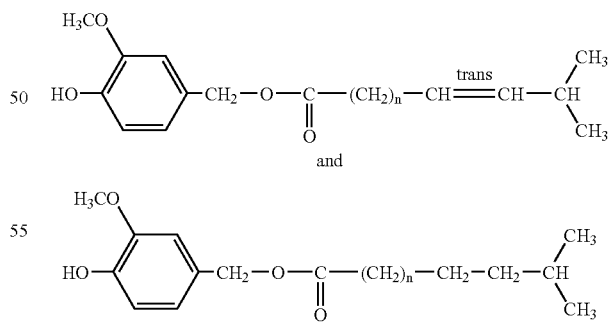

wherein n is an integer from 0 to 10.

* * * * *